United States Patent [19]

McGregor et al.

[11] Patent Number: 4,845,292
[45] Date of Patent: Jul. 4, 1989

[54] HYDROXY CONTAINING AMINES AS PHOSPHOLIPASE A2 INHIBITORS

[75] Inventors: William H. McGregor, Malvern; Lisa A. Marshall, Wayne; John H. Musser, Malvern, all of Pa.

[73] Assignee: American Home Products Corporation, New York, N.Y.

[21] Appl. No.: 143,776

[22] Filed: Jan. 13, 1988

[51] Int. Cl.⁴ .................... C07C 93/06; C07C 91/04; C07C 87/28; C07C 91/16
[52] U.S. Cl. .................................. 564/353; 564/503; 564/374; 564/355; 564/304
[58] Field of Search ............... 564/503, 374, 355, 353, 564/304

[56] References Cited
PUBLICATIONS

Chem. Abstracts, vol. 92 (No. 9) abst. No. 92:71044c Mar. 3, 1980.

Primary Examiner—John M. Ford
Assistant Examiner—Robert C. Whittenbaugh
Attorney, Agent, or Firm—George Tarnowski

[57] ABSTRACT

There are disclosed compounds of the formula

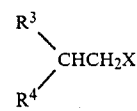

wherein

X is 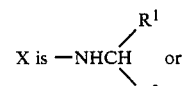 or

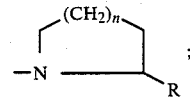

R is $-CH_2OH$ or $-CO_2R^3$;
$R^1$ is hydrogen, lower alkyl, lower alkoxy or hydroxybenzyl;
$R^2$ is hydroxyloweralkyl or diloweralkoxyalkyl;
$R^3$ is hydrogen or lower alkyl;
$R^4$ is alkyl of 10–20 carbons atoms, phenylalkyl of 11–18 carbon atoms or phenoxyalkyl of 11–18 carbon atoms; or
n is 1–3;

or a pharmaceutically acceptable salt thereof, and their use in the prevention and/or treatment of conditions such as allergic rhinitis, allergic bronchial asthma and other naso-bronchial obstructive air-passageway conditions, other immediate hypersensitivity reactions such as allergic conjunctivitis and various inflammatory conditions.

7 Claims, No Drawings

HYDROXY CONTAINING AMINES AS PHOSPHOLIPASE A2 INHIBITORS

The present invention is directed to a series of N-alkyl phenylalkyl and phenoxyalkylamino acid analogs having anti-inflammatory activity.

It is now well-established that arachidonic acid (AA) is metabolized in mammals by two distinct pathways. The metabolism of arachidonic acid by cyclooxygenase enzymes results in the production of prostaglandins and thromboxanes. The physiological activity of the prostaglandins has already been amply elucidated in recent years. It is now known that prostaglandins arise from the endoperoxides $PGG_2$ and $PGH_2$ by the cyclooxygenase pathway of arachidonic acid metabolism. These endoperoxides are also the precursors of the thromboxanes (Tx) $A_2$ and $B_2$. $TxA_2$ is a vasoconstrictor which stimulates platelet aggregation. In the normal situation, the vasoconstrictive and platelet aggregating properties of the thromboxanes are balanced by another product arising from the endoperoxides in the cyclooxygenase pathway, prostacyclin ($PGI_2$), which is a vasodilator with platelet aggregation inhibitory activity. In the event prostacyclin synthesis is impaired and/or platelet activation is enhanced, then thrombosis and vasoconstriction is favored. The role of prostanoids in haemostasis and thrombosis are reviewed by R. J. Gryglewski, *CRC Crit. Rev. Biochem.*, 7, 291 (1980) and J. B. Smith, *Am. J. Pathol.*, 99, 743 (1980). Cyclooxygenase metabolites are known to participate directly in the inflammatory response [see Higgs et al., Annals of Clinical Research, 16, 287-299 (1984)]. This is through their vasodepessor activities, participation in pain and fever augmentation of peptide mediator vascular permeability and edema forming properties. Finally, various aspects of cell mediated immunity are influenced by cyclooxygenase products.

The other pathway of AA metabolism involves lipoxygenase enzymes and results in the production of a number of oxidative products called leukotrienes. The latter are designated by the LT nomenclature system, and the most significant products of the lipoxygenase metabolic pathway are the leukotrienes $B_4$, $C_4$ and $D_4$. The substance denominated slow-reacting substance of anaphylaxis (SRS-A) has been shown to consist of a mixture of leukotrienes, with $LTC_4$ and $LTD_4$ as the primary products and having varying amounts of other leukotriene metabolites [see Bach et al., *J. Immum.*, 215, 115-118 (1980); *Biochem. Biophys. Res. Commun.*, 93, 1121-1126 (1980)].

The significance of these leukotrienes is that a great deal of evidence is accumulating showing that leukotrienes participate in inflammatory reactions, exhibit chemotactic activities, stimulate lysosomal enzyme release and act as important factors in the immediate hypersensitivity reaction. It has been shown that $LTC_4$ and $LTD_4$ are potent bronchoconstrictors of the human bronchi [see Dahlen et al., *Nature*, 288, 484-486 (1980)], and another leukotriene, $LTB_4$, is a powerful chemotactic factor for leukocytes [see A. W. Ford-Hutchinson, *J. Roy. Soc. Med.*, 74, 831-833 (1981)]. The activity of leukotrienes and slow-reacting substances as mediators of inflammation and hypersensitivity is extensively reviewed in Bailey and Casey, *Ann. Reports Med. Chem.*, 17, 203-217 (1982).

Phospholipase $A_2(PLA_2)$ is the critical rate limiting enzyme in the arachidonic acid (AA) cascade since it is responsible for the hydrolysis of esterified AA from the C-2 position of membrane phospholipids. This reaction generates two products (1) free AA which is then available for subsequent metabolism by either the cyclooxygenase or lipoxygenase enzymes and (2) lysophospholipid. When alkyl-arachidonoyl-glycerophosphatidylcholine is acted upon by the $PLA_2$ the generation of platelet activating factor (PAF) is initiated; PAF is pro-inflammatory in its own right [see Wedmore et al., Br. J. Pharmacol., 74, 916-917 (1981)]. In this regard it may be noted that the anti-inflammatory steroids are thought to inhibit eicosanoid synthesis by inducing the synthesis of a $PLA_2$ inhibitory protein denominated macrocortin or lipomodulin [see Flower et al., *Nature, London*, 278, 456 (1979) and Hirata et al., *Proc. Natn. Acad. Sci. U.S.A.*, 77, 2533 (1980)].

As the initial step leading to subsequent conversion of AA to the various eicosanoids by the cyclooxygenase and lipoxygenase pathways, the $PLA_2$-mediated release of AA from membrane phosholipids is a critical event in attempting to deal with the various physiological manifestations which are based on the activity of the eicosanoids and/or PAF. Thus, while $PLA_2$ has been shown to be required for platelet aggregation [Pickett et al., *Biochem., J.* 160, 405 (1976)], cardiac contraction and excitation [Geisler et al., *Pharm. Res. Commun.*, 9, 117 (1977)], as well as prostaglandin synthesis [Vogt, Adv. Prostagl. Thromb. Res., 3, 89 (1978)], the inhibition of $PLA_2$ is indicated in the therapeutic treatment of both PAF induced or cyclooxygenase and/or lipoxygenase pathway product-mediated physiological conditions. Thus, $PLA_2$ inhibitors are a rational approach to the prevention, removal or amelioration of such conditions as allergy, anaphylaxis, asthma and inflammation.

The invention provides novel compounds of the formula

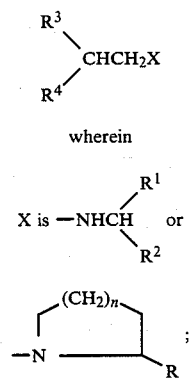

wherein

X is $-NHCH\begin{subarray}{l}R^1\\R^2\end{subarray}$ or

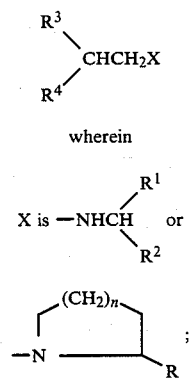

R is $-CH_2OH$ or $-CO_2R^3$;
$R^1$ is hydrogen, lower alkyl, lower alkoxy or hydroxybenzyl;
$R^2$ is hydroxyloweralkyl or diloweralkoxyalkyl;
$R^3$ is hydrogen or lower alkyl;
$R^4$ is alkyl of 10-20 carbon atoms, phenylalkyl of 11-18 carbon atoms or phenoxyalkyl of 11-18 carbon atoms;
n is 1-3;
or a pharmaceutically acceptable salt thereof.

The terms "lower alkyl" and "lower alkoxy," when used alone or in combination, refer to moieties having 1-6 carbon atoms in the carbon chain.

The compounds of the invention can be prepared by the following reaction scheme

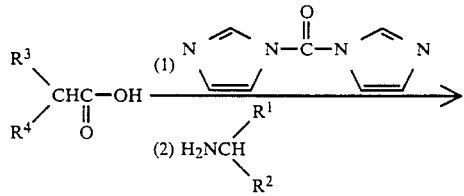
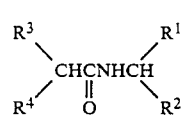

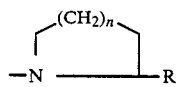

wherein the carboxylic acid starting material is initially reacted with carbonyl diimidazole in an organic solvent, preferably dried tetrahydrofuran followed by reaction of the intermediate so formed with the amine reactant $H_2NCHR^1R^2$ to form the amide of the desired final product. The final step in the preparation scheme involves reduction of the amides by diborane reduction. The amides are reduced using diborane as a solution in tetrahydrofuran to yield the desired final product amines.

Compounds in which X is

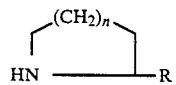

can be prepared by the above-outlined reaction using

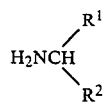

in place of the

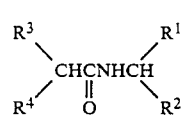

reactant.

The starting materials used in the preparation of the compounds of the invention are commercially available or can be prepared by conventional procedures taught in the chemical literature. Thus, starting carboxylic acids such as octadecanoic, phenyldecanoic, phenyloctanoic, phenoxyundecanoic and phenylhexanoic are commercially available. In like manner, the starting $H_2NCHR^1R^2$ compounds, such as norleucine methyl ester, 2,2-diethoxyethylamine, tyrosine methyl ester and proline methyl ester are either commercially available or can be prepared by known preparative schemes conventional in the chemical arts. It is also possible to use the amino alcohols as the $H_2NCHR^1R^2$ starting materials, as for example norleucinol (2-amino-1-hexanol), tyrosinol or prolinol.

The compounds of the invention, by virtue of their asymmetric configuration, exhibit chirality. Accordingly, the compounds of the invention include those designated as in the natural (L or S) or unnatural (D or R) configuration or the racemates thereof.

The compounds of the invention are capable of forming pharmaceutically acceptable salts, including the salts of pharmaceutically acceptable organic and inorganic acids such as hydrochloric, hydrobromic, sulfuric, nitric, phosphoric, methanesulfonic, benzenesulfonic, acetic, citric, fumaric, maleic, malic, succinic and the like.

The compounds of the invention, by virtue of their ability to inhibit activity of $PLA_2$ enzyme, are useful in the treatment of conditions mediated by products of the oxidation of arachidonic acid. Accordingly, the compounds are indicated in the prevention and treatment of such conditions as allergic rhinitis, allergic bronchial asthma and other naso-bronchial obstructive air-passageway conditions, other immediate hypersensitivity reactions, such as allergic conjunctivitis; and various inflammatory conditions such as those present in rheumatoid arthritis, osteoarthritis, tendinitis, bursitis, psoriasis (and related skin inflammation) and the like.

When the compounds of the invention are employed in the treatment of allergic airways disorders or in anti-inflammatory therapy, they can be formulated into oral dosage forms such as tablets, capsules and the like. The compounds can be administered alone or by combining them with conventional carriers, such as magnesium carbonate, magnesium stearate, talc, sugar, lactose, pectin, dextrin, starch, gelatin, tragacanth, methylcellulose, sodium carboxymethylcellulose, low melting wax, cocoa butter and the like. Diluents, flavoring agents, solubilizers, lubricants, suspending agents, binders, tablet-disintegrating agents and the like may be employed. The compounds may be encapsulated with or without other carriers. In all cases, the proportion of active ingredients in said compositions both solid and liquid will be at least to impart the desired activity thereto on oral administration. The compounds may also be injected parenterally, in which case they are used in the form of a sterile solution containing other solutes, for example, enough saline or glucose to make the solution isotonic. For administration by inhalation or insufflation, the compounds may be formulated into an aqueous or partially aqueous solution, which can then be utilized in the form of an aerosol. The compounds may also be used topically and for this purpose they may be formulated in the form of dusting powders, creams or lotions in pharmaceutically acceptable vehicles, which are applied to affected portions of the skin.

The dosage requirements vary with the particular compositions employed, the route of administration, the severity of the symptoms presented and the particular subject being treated. Treatment will generally be initiated with small dosages less than the optimum dose of the compound. Thereafter the dosage is increased until the optimum effect under the circumstances is reached. In general, the compounds of the invention are most desirably administered at a concentration that will generally afford effective results without causing any harmful or deleterious side effects, and can be administered either as a single unit dose, or if desired, the dosage may be divided into convenient subunits administered at suitable times throughout the day.

The standard pharmacological procedures, which are described fully in the examples given hereafter, measure the ability of the compounds of the invention to inhibit the activity of $PLA_2$ enzyme in vitro; measure the in vivo activity of the compounds as anti-inflammatory agents in the rat carrageenan paw edema assay; and determine the specificity of action of the $PLA_2$ inhibitors of the invention as measured by their ability to inhibit the synthesis of $LTB_4$ and $TxB_2$ by rat glycogen-elicited polymorphonuclear leukocytes.

EXAMPLE 1

2-(Octadecylamino)-1-hexanol, hydrochloride 1 meq. (0.284 g) of octadecanoic acid and 1 meq. (0.162 g) of carbonyl diimidazole are combined in 5 ml of molecular sieve-dried tetrahydrofuran and reacted for 1.5 hours at ambient temperature. To this reaction mixture is added 1 meq. (0.145 g) L-norleucine methyl ester in tetrahydrofuran at 0° C. over a period of 10-20 minutes, and reacted overnight at ambient temperature. The tetrahydrofuran is then removed under reduced pressure and the residue dried in vacuo.

The protected product so obtained is purified by silica gel chromatography (2×100 cm column, 3.5 ml fractions) in a 10:1 methylene chloride:methanol solvent system and the purified product is dried in vacuo at ambient temperature.

Reduction of the amide intermediate obtained thereby is accomplished by refluxing 1 meq. of the amide with 2.5 meq. of 1N diborane in tetrahydrofuran for 1 hour and further reacting overnight at ambient temperature. After reaction, the solvent is removed in a stream of nitrogen and 1N HCl is added and the solution is stirred overnight at ambient temperature. Solid potassium carbonate is added to pH >10, extracted 2× with ethyl ether or ethyl acetate and dried over sodium sulfate. The amine hydrochloride is prepared by adding saturated HCl in ethyl acetate to the above solution until acid, adding ethyl ether and cooling to 4° C. The resulting crystals are filtered, washed with ethyl ether and dried in vacuo to yield 1.0 g of title product having a melting point of 137°-39° C. (uncorr.).

Analysis for: $C_{24}H_{51}NO.HCl$: Calculated: C, 70.48; H, 12.91; N, 3.45; Cl, 8.73. Found: C, 70.45; H, 12.41; N, 3.67; Cl, 8.97.

IR: KBr 1470, 1570, 2850, 2920.

NMR: 0.90 (t, $3H-CH_3$), 1.30 (s, aliphatic $CH_2$), 1.85 (t, $CH-CH_2$), 3.1 (m, $CH_2-NH$), 3.9 (t, $CH-NH$), Ca 4.2 ($CH_2OH$).

EXAMPLE 2

Following the procedure of Example 1, using L-norleucine methyl ester and 10-phenyldecanoic acid, 8-phenyloctanoic acid and 6-phenylhexanoic acid, respectively, there are prepared the following:

(a) 2-[(10-Phenyldecyl)amino]-1-hexanol, hydrochloride

Yield: 230 mg; melting point 112.5°-114.5° C. (uncorr.).

Analysis for: $C_{22}H_{39}NO.HCl$: Calculated: C, 71.41; H, 10.90; N, 3.79; Cl, 9.58. Found: C, 71.61; H, 10.85; N, 3.89; Cl, 9.16.

IR: 1015, 1465, 1560, 2930, 3320.

NMR: 0.9 (t, $3H, CH_3$), 1.3 (br. S. aliphatic $CH_2$), ca. 1.8 (an $CH-CH_2$),

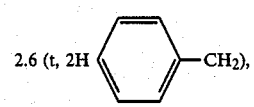

ca. 3.1 (m, 2H, $CH_2-NH$), ca 3.8 (m, $CH_2-OH$, CHNH),

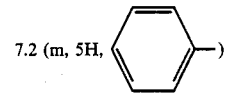

(b) (S)-2[(8-Phenyloctyl)amino]-1-hexanol, hydrochloride

Yield: 680 mg; melting point 104°-106° C. (uncorr.).

Analysis for: $C_{20}H_{35}NO.HCl$: Calculated: C, 70.25; H, 10.61; N, 4.10; Cl, 10.37. Found: C, 70.13; H, 10.31; N, 4.54; Cl, 9.97.

IR: 700, 750, 1465, 1555, 2930, 3350

NMR: 0.9 (t, $3H, CH_3$), 1.35 (S, aliphatic $CH_2$), 1.75 ($CH-CH_2$),

3.0 ($CH_2-NH$), 3.9 (t, $CHNH, CH_2OH$), 7.2 (aromatic H), 8.9 ($-NH$).

(c) 2-[(6-Phenylhexyl)amino]-1-hexanol, hydrochloride

Yield: 1 g; melting point 82°-84° C. (uncorr.).

Analysis for: $C_{18}H_{31}NO.HCl$: Calculated: C, 68.87; H, 10.27; N, 4.46; Cl, 11.29. Found: C, 70.10; H, 10.52; N, 4.66; Cl, 10.54.

IR: 700, 1450, 1550, 2840, 2920, 3300.

NMR: 0.9 (t, $3H, CH_3$), 1.4 (br. singlet aliphatic $CH_2$),

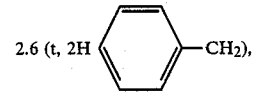

3.1 (m, 2H, $CH_2NH$), 7.2 (aromatic H).

EXAMPLE 3

Following the procedure of Example 1, and using 11-phenoxyundecanoic acid and (S)-2-pyrrolidinemethanol (L-prolino), DL-proline methyl ester or norleucine methyl ester, there are prepared the following compounds:

(a) (S)-1-(11-phenoxyundecyl)-2-pyrrolidinemethanol, hydrochloride

Yield: 3.5 g; melting point 90°-92° C. (uncorr.).

Analysis for: $C_{22}H_{37}NO_2.HCl$: Calculated: C, 68.60; H, 10.91; N, 3.61; Cl, 9.14. Found: C, 68.28; H, 9.71; N, 3.62; Cl, 10.24.

IR: 695, 755, 1245, 1470, 1490, 1585, 2850, 2920.

NMR: 1.3 (S, aliphatic $CH_2$), 2.0 (m, $CH-CH_2$), 2.9 (m, $CH-N$), 3.9 (m, $CH-N, CH_2OH$),

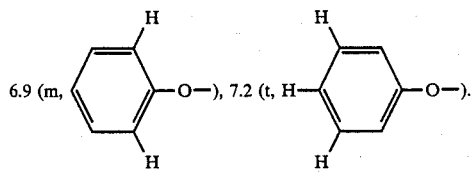

(b) 1-(11-Phenoxyundecyl)-DL-proline methyl ester, hydrochloride

Yield: 340 mg; melting point 54°-55° C. (uncorr.).
Analysis for: $C_{23}H_{37}NO_3 \cdot HCl$: Calculated: C, 66.45; H, 9.26; N, 3.57; Cl, 8.63. Found: C, 67.21; H, 9.07; N, 3.41; Cl, 9.00.
IR: 700, 765, 1250, 1755, 2940.
NMR: 1.3 (S aliphatic $CH_2$), 3.9 (m, CH—NH),

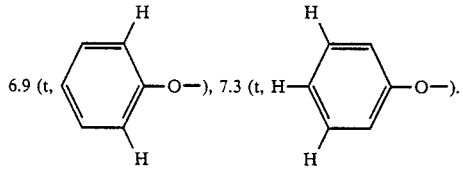

(c) (S)-2-[(11-Phenoxyundecyl)amino]-1-hexanol, hydrochloride

Yield: 1.2 g.
Analysis for: $C_{23}H_{41}NO_2 \cdot HCl$: Calculated: C, 69.06; H, 10.58; N, 3.52; Cl, 8.86. Found: C, 68.98; H, 10.54; N, 3.45; Cl, 8.87.
IR: 685, 750, 1255, 1495, 1595, 2910.
NMR: 0.9 (t, 3H, $CH_3$), 1.4 (S, aliphatic $CH_2$), 1.75 (m, HC—$CH_2$), 3.0 (m, $CH_2$—NH), 3.8–4.2 (m, $CH_2$—OH, CHNH),

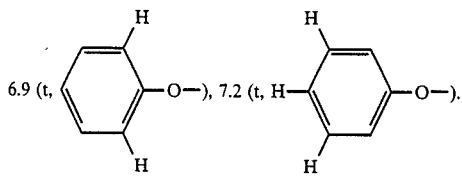

EXAMPLE 4

N-(2,2-diethoxyethyl)-11-phenoxyundecanamine, hydrochloride

Following the procedure of Example 1 and using 11-phenoxyundecanoic acid and 2,2-diethoxyethylamine, there is prepared the title compound in 500 mg yield with a melting point of 95°-98° C. (uncorr.).
Analysis for: $C_{23}H_{41}NO_3 \cdot HCl$: Calculated: C, 66.40; H, 10.17; N, 3.37; Cl, 8.52. Found: C, 66.24; H, 10.13; N, ;b 3.42; Cl, 9.15.
IR: 750, 1250, 1470, 1595, 2910.
NMR: 1.3 (m, aliphatic $CH_2$ and $CH_3$), 1.8 (m, CH—$CH_2$), 3.1 (q, $CH_2$—NH), 3.7 (m, CH—O—$CH_2$),

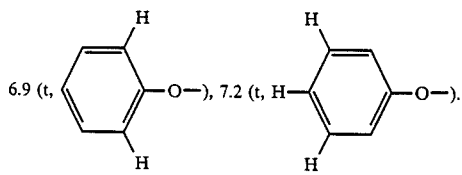

EXAMPLE 5

(S)-4-hydroxy-α-[(10-phenyldecyl)amino]benzenepropanol, hydrochloride

Following the procedure of Example 1 and using 10-phenyldecanoic acid and L-tyrosinol, there is prepared the title compound in 3.1 g yield with a melting point of 95°-97° C. (uncorr.).
Analysis for: $C_{25}H_{37}NO_2 \cdot HCl$: Calculated: C, 71.49; H, 9.12; N, 3.33; Cl, 8.44. Found: C, 71.18; H, 9.24; N, 3.24; Cl, 8.05.
IR: 700, 740, 1225, 1260, 1515, 1570, 1615, 2850, 2930.
NMR: 1.2 (S, aliphatic $CH_2$),

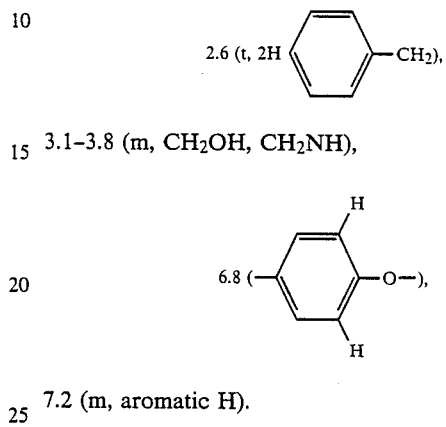

7.2 (m, aromatic H).

EXAMPLE 6

The ability of the compounds of the invention to inhibit the activity of cell free human platelet $PLA_2$ enzyme is measured in the following in vitro assay.
The assay is carried out as follows:
Substrate Preparation
*E. coli*, cultured to exponential growth, are sedimented for 15 minutes at 10,000 g and resuspended in sterile isotonic saline (1–3 ml). 10–25 μCi uniformly labeled [$^3$H]-arachidonic acid (AA) is added to a sterile flask, evaporated by $N_2$ and resolubilized with 0.3 ml 20% fatty acid-free bovine serum albumen (BSA). 75–100 ml of nutrient broth and 1 ml *E. coli* are then added to each flask and incubated for 2–3 hours at 37° C. [$^3$H]-AA labelled *E. coli* are then sedimented, suspended in saline and added to fresh nutrient broth and incubated for 1.5 hours at 37° C. to complete [$^3$H]-AA incorporation into the phospholipids. After overnight refrigeration of cultures, *E. coli* are again sedimented, suspended in saline and autoclaved for 15 minutes at 120° C. *E. coli* cultures are washed twice with saline (first wash contains 1% BSA) and resuspended in saline. Non-labelled *E. coli* cultures are also prepared in the same manner. Cell number is determined by measuring the optical density at 550 nm ($3 \times 10$ cell/ml = 1 O.D.). The amount of radioactivity associated with cells is determined by counting a defined volume of cell suspension. The specific activity is subsequently adjusted by adding non-labelled *E. coli* to yield 10,000 cpm/10 mmols of *E. coli*/25 ml.

Platelet $PLA_2$ Preparation

Expired human platelets from the blood bank are centrifuged for 15 minutes at 200 g to obtain a platelet rich fraction and to remove the red blood cells. Platelets are sedimented for 15 minutes at 2500 g and the plasma is removed before adding cold 0.18N $H_2SO_4$ (4ml/unit). Platelets are homogenized, incubated for 1 hour at 4° C., homogenized again and centrifuged for 15 minutes at 10,000 g. The $PLA_2$ enriched supernatant fluid is removed and the amount of protein is determined by the Lowry method. The preparation is divided into various portions and stored at −20° C.

Assay of PLA$_2$ Activity

The assay measures the hydrolysis of *E. coli* membrane phospholipids via the release of free [$^3$H]-AA from the C-2 position of phospholipids by human platelet PLA$_2$. To ice cold 15×100 mm test tubes, the following additions are made; 2.5×10$^8$ *E. coli* (equivalent to 5 nmol phospholipid), 5 mM Ca$^{++}$, 100 mM Tris buffer (pH=7.4), 100 μg platelet extract (or an amount to produce 20–30% hydrolysis), drug or vehicle. Incubations are carried out at 37° C. in a shaking water bath for 30 minutes. The reaction is terminated by the addition of 2 volumes of tetrahydrofuran (THF) and the mixture is vortexed. Hydrolyzed [$^3$H]-AA is separated from unhydrolyzed phospholipid by solid phase extraction using Bond elute NH$_2$ columns (Analytichem Internat.). Columns are conditioned with 0.5 ml THF followed by 0.5 ml THF:H$_2$O (2.0:0.1 ml/v/v). Samples are loaded onto columns and hydrolyzed [$^3$H]-AA is eluted with 1 ml THF:glacial acetic acid (98.0:2.0 ml v/v). The eluant is transferred to vials, 10 ml Optifluor is added and the radioactivity is determined by liquid scintillation counting.

Treatments are corrected for non-enzymatic hydrolysis by subtracting the dpms in treatments containing no enzyme Mean [$^3$H]-AA dpm is determined and a percent inhibition relative to vehicle treated samples is calculated.

The percent hydrolysis is calculated by the following equation:

$$\% \text{ Hydrolysis} = \frac{\text{free fatty acid } (dpm)}{\text{total phospholipid + free fatty acid } (dpm)}$$

Rate of Hydrolysis =

$$\frac{\% \text{ hydrolysis} \times \text{total phospholipid content (5 nmol)}}{\text{incubation time (min)}}$$

Activity of standard drugs:

| Drug | Inhibition of PLA$_2$ Activity IC$_{50}$, μM |
|---|---|
| para-Bromophenacyl bromide | 23.7 |
| Arachidonic Acid | 10.1 |

When tested in the above-described assay, the compounds of the invention gave the following results:

TABLE 1

| Compound of Example No. | IC$_{50}$, μM |
|---|---|
| 1 | 12 |
| 2a | 19 |
| 2b | 45 |
| 2c | >100 |
| 3a | 17 |
| 3b | 63 |
| 4 | 33 |
| 5 | 48 |

The results show the compounds of the invention to have PLA$_2$ inhibitory activity in the assay in question.

EXAMPLE 7

The compounds 5- and 12-hydroxyeicosatetraenoic acid (5-HETE and 12-HETE) and LTB$_4$ are early arachidonic acid oxidation products in the lipoxygenase cascade, which have been shown to mediate several aspects of inflammatory and allergic response. This is especially true with respect to 5,12-diHETE, which is also denoted as LTB$_4$ [see Ford-Hitchinson, *J. Roy. Soc. Med.*, 74, 831 (1981)]. Compounds which inhibit the PLA$_2$-mediated release of arachidonic acid thereby effectively prevent the oxidation of arachidonic acid to the various leukotriene products via the lipoxygenase cascade. Accordingly, the specificity of action of PLA$_2$ inhibitors can be determined by the activity of test compounds in this assay, which measures the ability of compounds to inhibit the synthesis of LTB$_4$ by rat glycogen-elicited polymorphonuclear leukocytes (PMN) in the presence of exogenous substrate.

The assay is carried out as follows:

Rat polymorphonuclear leukocytes (PMNs) are obtained from female Wistar rats (150-200 g) which receive an injection of 6% glycogen (10 ml i.p.). Rats are sacrificed 18–24 hours post injection by CO$_2$ asphyxiation and the elicited cells are harvested by peritoneal lavage using physiological saline (0.9% NaCl). The exudate is centrifuged at 400×g for 10 minutes. The supernatant fluid is discarded and the cell pellet is resuspended to a concentration of 2.0×10$^7$ cells/ml in HBSS containing Ca$^{++}$ and Mg$^{++}$ and 10 μM L-cysteine.

To 1 ml aliquots of cell suspension, test drugs or vehicle are added, then preincubated at 37° C. for 10 minutes. A23187 (1 μM), [$^3$H]-AA (3.0 μCi/ml) and unlabeled AA (1 μM) are then added and the samples are further incubated for 10 minutes. The reaction is terminated by centrifugation and pelleting cells. Supernatants are then analyzed by HPLC analysis on a 15 cm×4.6 mm ID Supelcosil LC-18 (Supelco)(3M) column, using a two solvent system at a flow rate of 1.4 ml total flow as follows:

Solvent A: 70:30 17.4 mM H$_3$PO$_4$:CH$_3$CN
Solvent B: CH$_3$CN
Gradient: (system is equillibrated with Solvent A)

| Time | Percent A | Percent B |
|---|---|---|
| 0 | 100 | 0 |
| 15.0 | 100 | 0 |
| 20.0 | 65 | 35 |
| 40.0 | 65 | 35 |
| 42.0 | 10 | 90 |
| 50.0 | 10 | 90 |
| 50.1 | 100 | 0 |

Percent solvent changes are accomplished in a linear fashion.

Injections: 150 μl of each supernatant is injected directly onto column and $^3$H arachidonic acid metabolites are monitored using an on-line radioactivity detector (Ramona, IN/US, Fairfield, NJ).

Standards: 10$^4$–2.0×10$^4$ dpm of eicosanoids of interest are injected in 90 μl EtOH cocktail.

Co-chromatography with standard [$^3$H] leukotriene B$_4$ (LTB$_4$) in medium of stimulated PMN exposed to drug is compared to that found in medium of stimulated cells exposed to no drug, generating percent inhibition.

Results are expressed as percent inhibition at a given compound dose.

Testing compounds of the invention in this assay give the following results:

TABLE 2

| Compound of Example Number | % Inhibition (at 10 μM) |
|---|---|
| 1 | 24 |
| 2a | 89 |
| 2b | 52 (at 5 μM) |

TABLE 2-continued

| Compound of Example Number | % Inhibition (at 10 μM) |
|---|---|
| 2c | 16 |
| 3a | 0 |

EXAMPLE 8

The procedure of Example 7 is also employed for the determination of the extent to which compounds of the invention inhibit the synthesis of the arachidonic acid cyclooxygenase oxidation product $TxB_2$.

In this assay, the procedure of Example 7 is carried out as described. However, in order to determine cyclooxygenase activity, the samples are co-chromatographed with authentic reference $[^3H]$-$TxB_2$.

The results are calculated as in Example 7 and presented below:

TABLE 3

| Compound of Example Number | % Inhibition (at 10 μM) |
|---|---|
| 1 | 26 |
| 2a | 73 |
| 2b | 0 (at 5 μM) |
| 2c | 24 |
| 3a | 37 |

EXAMPLE 9

The compounds in the scope of the invention are further tested in the rat carrageenan paw edema to determine their ability to inhibit the acute inflammatory response.

This assay is carried out as follows:

140–180 mg male Sprague-Dawley rats, in groups of 6 animals are injected subcutaneously in the right paw with 0.1 ml of 1% carrageenan at zero time. Mercury plethysmographic readings (ml) of the paw are made at zero times and 3 hours later. Test compounds are suspended or dissolved in 0.5% methylcellulose and given perorally 1 hour prior to carrageenan administration.

The increase in paw volume (edema in ml.) produced by the carrageenan is measured. Paw edema is calculated (3 hour volume minus zero time volume), and percent inhibition of edema is determined. Unpaired Student's t-test is used to determine statistical significance.

The activity of standard drugs in this assay is as follows:

| Drug | Oral $ED_{50}$ (95% C.L.) mg/kg |
|---|---|
| Indomethacin | 3.7 (0.6, 23.8) |
| Aspirin | 145.4 (33.1, 645.6) |
| Phenylbutazone | 26.2 (2.3, 291.0) |

When tested in this assay, the compounds of the invention gave the following results:

TABLE 5

| Compound of Example No. | % Inhibition at 50 mg/kg (peroral) |
|---|---|
| 1 | 26 |
| 2a | 39 |
| 2b | 25 |
| 2c | 34 |
| 3a | 26 |
| 4 | 34 |

The results show that the compounds tested have oral activity in the rat carrageenan paw edema assay, evidencing an effect on the acute inflammatory response.

What is claimed is:

1. A compound having the formula

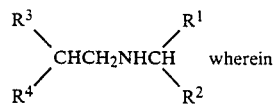 wherein $R^1$ is hydrogen, lower alkyl, lower alkoxy or hydroxybenzyl;

$R^2$ is hydroxyloweralkyl or diloweralkoxyalkyl;

$R^3$ is hydrogen or lower alkyl;

$R^4$ is phenylalkyl of 11–18 carbon atoms or phenoxyalkyl of 11–18 carbon atoms;

or a pharmaceutically acceptable salt thereof.

2. The compound of claim 1, having the name 2-[(10-phenyldecyl)amino]-1-hexanol.

3. The compound of claim 1, having the name (S)-2-[(8-phenyloctyl)amino]-1-hexanol.

4. The compound of claim 1, having the name 2-[(6-phenylhexyl)amino]-1-hexanol.

5. The compound of claim 1, having the name (S)-2-[(11-phenoxyundecyl)amino]-1-hexanol.

6. The compound of claim 1, having the name N-(2,2-diethoxyethyl)-11-phenoxyundecanamine.

7. The compound of claim 1, having the name (S)-4-hydroxy-α-[(10-phenyldecyl)amino]benzenepropanol.

* * * * *